US012758390B2

(12) United States Patent
Kim et al.

(10) Patent No.: US 12,758,390 B2
(45) Date of Patent: Oct. 13, 2026

(54) FEMORAL STEM DESIGN METHOD

(71) Applicant: Corentec Co. Ltd., Seoul (KR)

(72) Inventors: Sang-Min Kim, Seoul (KR); Kwan-Kyu Park, Seoul (KR); Kee-Hyung Rhyu, Seoul (KR); Jeong-Joon Yoo, Seoul (KR); Seung-Jae Lim, Seoul (KR); Young-Wook Lim, Seoul (KR); Seung-Beom Han, Seoul (KR); Jung-Sung Kim, Seoul (KR); Tae-Jin Shin, Hanam-si (KR)

(73) Assignee: CORENTEC CO., LTD., Seoul (KR)

( * ) Notice: Subject to any disclaimer, the term of this patent is extended or adjusted under 35 U.S.C. 154(b) by 670 days.

(21) Appl. No.: 18/258,381

(22) PCT Filed: Dec. 14, 2021

(86) PCT No.: PCT/KR2021/018995
§ 371 (c)(1),
(2) Date: Jun. 20, 2023

(87) PCT Pub. No.: WO2022/145814
PCT Pub. Date: Jul. 7, 2022

(65) Prior Publication Data

US 2024/0374393 A1 Nov. 14, 2024

(30) Foreign Application Priority Data

Dec. 31, 2020 (KR) ........................ 10-2020-0189942

(51) Int. Cl.
*A61F 2/38* (2006.01)
*A61B 34/10* (2016.01)
*A61F 2/30* (2006.01)

(52) U.S. Cl.
CPC ........ *A61F 2/3859* (2013.01); *A61F 2/30942* (2013.01); *A61B 2034/108* (2016.02)

(58) Field of Classification Search
CPC ................ A61F 2/3859; A61F 2/30942; A61F 2002/30616; A61F 2002/30948;
(Continued)

(56) References Cited

U.S. PATENT DOCUMENTS 5,824,085 A 10/1998 Alind et al.
7,749,278 B2 7/2010 Frederick et al.
(Continued)

FOREIGN PATENT DOCUMENTS

KR 10-0917715 B1 9/2009
KR 10-2011-0006208 A 1/2011
(Continued)

OTHER PUBLICATIONS

International Search Report and Written Opinion dated Apr. 12, 2022, issued in PCT Application No. PCT/KR2021/018995, filed Dec. 14, 2021.

*Primary Examiner* — Yashita Sharma
(74) *Attorney, Agent, or Firm* — Workman Nydegger

(57) ABSTRACT

A femoral stem design method includes: a data collection step of collecting femur data from a plurality of patients; a measurement standard setting step of setting a standard for designing a femoral stem with respect to the femur data of the plurality of patients; a measurement step of measuring a predetermined part of a femur from the plurality of femur data; a dimension determination step of determining dimensions of each part of a plurality of implants to be inserted into the femur; and a shape determination step of determining shapes of the plurality of implants according to the dimensions of the plurality of implants, wherein the measurement standard setting step includes a boundary setting
(Continued)

step of setting a boundary that distinguishes cortical bone and cancellous bone from the femur data of the plurality of patients, and an axis setting step of setting an axis extending from the proximal part to the distal part of the femur.

12 Claims, 11 Drawing Sheets

(58) Field of Classification Search
CPC ...... A61F 2002/4633; A61F 2/30; A61F 2/36; A61F 2/3609; A61F 2/3662; A61F 2/4657; A61F 2/30739; A61F 2002/3096; A61B 2034/108; A61B 34/10; A61B 2034/102; A61B 2034/105
See application file for complete search history.

(56) References Cited

U.S. PATENT DOCUMENTS

| | | | | |
|---|---|---|---|---|
| 2011/0029116 | A1 | 2/2011 | Jordan et al. | |
| 2013/0197866 | A1* | 8/2013 | Wuestemann ....... | A61B 17/155 703/1 |
| 2015/0328004 | A1 | 11/2015 | Mafhouz | |

FOREIGN PATENT DOCUMENTS

| | | | |
|---|---|---|---|
| WO | 98/14128 | A1 | 4/1998 |
| WO | 2009/076296 | A1 | 6/2009 |
| WO | 2015/057898 | A1 | 4/2015 |

* cited by examiner (a)

(b)

FEMORAL STEM DESIGN METHOD

TECHNICAL FIELD

The present disclosure relates generally to a femoral stem design method. More particularly, the present disclosure relates to a femoral stem design method including a data collection step of collecting femur data from a plurality of patients, a measurement standard setting step of setting a standard for designing a femoral stem with respect to the femur data of the plurality of patients collected in the data collection step, a measurement step of measuring a predetermined part of the femur from the femur data of the plurality of patients, a dimension determination step of determining a dimension of each part of a plurality of implants to be inserted into the femur, and a shape determination step of determining shapes of the plurality of implants according to the dimension of the plurality of implants determined in the dimension determination step, in which the measurement standard setting step includes a boundary setting step of setting a boundary that distinguishes the cortical bone and the cancellous bone from the femur data of the plurality of patients, and an axis setting step of setting an axis extending from the proximal part to the distal part of the femur. Thereby, during the design of an artificial femoral stem to be inserted into the femur in surgical procedures such as hip arthroplasty, data analysis can be quickly carried out by using minimal anatomical data through a patient's 2D-based human anatomical information, and implants can be designed to have regular shapes corresponding to the anatomical shape of the patient's femur.

BACKGROUND ART

In artificial hip arthroplasty, an artificial femoral stem implant is inserted into the femur to replace the damaged bone. Artificial femoral stems of various sizes are required according to the size of the patient's femur. Conventional implant sets cannot accurately reflect the shape of bones of various sizes. For example, a larger femur does not mean that it is simply enlarged from a smaller femur in the same proportion. Therefore, an implant set obtained by simply enlarging implants of a specific size in the same proportion does not necessarily reflect the actual shape of femurs of various sizes. For this reason, the implant set made according to the traditional methodology may not be suitable for insertion into the patient's femur in some cases and may cause surgical failure and side effects.

FIG. 1 illustrates a femoral stem family disclosed in U.S. Pat. No. 7,749,278. In the femoral stem family, a medial part of each femoral stem has a constant shape, and a lateral part thereof has a shape that increases as the size of the femoral stem increases. While the femoral stem family of this structure is easy to design, it does not fit the shape of the femur, which is different for each patient, so there arises a problem in that the femoral stem is shaken or rotated within the femur during insertion. This is due to the fact that the medial part of the femoral stem does not correspond to the shape of the patient's femur.

FIG. 2 illustrates a femoral stem implant inserted into the femur. Referring to FIG. 2, for insertion of a femoral stem in artificial hip arthroplasty, the relatively hard cancellous bone is removed, and then the femoral stem is inserted into the cavity in the femur. The femur roughly consists of the femoral shaft 91, the femoral head 93, and the lesser trochanter 95 located medially to the femoral shaft 91. The femoral shaft 91 is divided into the cortical bone 911 and the cancellous bone 913. The cortical bone 911 is located in the outer layer of the bone and is a hard area with no cavity. The cancellous bone 913 is located inside the cortical bone 911, and consists of bony trabeculae, and marrow cavities that contain adipose tissue or hematopoietic tissue. Since the shape of the femur after removing the cancellous bone can be different for each patient, the shape of the femoral stem and the shape of the inside of the femur have to match as much as possible. However, the femoral stem implant set enlarged in the same proportion as described above cannot correspond to the inner shape of the patient's femur.

In particular, in the case of a femoral stem implant inserted into the femur from the proximal side of the patient's femur, it may be important which side of the implant comes in contact with the bone. When the implant is designed to come into contact with the bone on its proximal side, the implant can be easily press-fitted into the femur and fixed within the femur. On the contrary, when the implant is designed to come into contact with the bone on its distal side, the distal part of the implant may come into contact with the inside of the bone during insertion, making it difficult to press-fit the implant. Also, due to the nature of the femoral stem implant connected to the acetabular cup from the proximal side, it is difficult to fix the implant in position within the bone.

In an effort to solve the above problems, there has been proposed a method of designing a femoral stem implant set by obtaining patient's 3D data through CT and MRI of the patient's femur, setting cross-sections at intervals of equal to or less than 10 mm, and measuring dimensions such as width and area of the femur from the cross-sections. However, the disadvantage of this method is that it consumes a lot of time and cost in analyzing the patient's anatomical dimensions, and it cannot provide a reasonable design basis for the shape of the femoral stem by size because it is a method of designing the implant set by simply measuring dimensions from 3D data.

Accordingly, there is a demand in the industry for a femoral stem design method that designs a shape more economically and quickly using minimal anatomical data, and preferably determines an implant shape that corresponds to the inner shape of the patient's femur.

DISCLOSURE

Technical Problem

Accordingly, the present disclosure has been made keeping in mind the above problems occurring in the related art, and an objective of the present disclosure is to provide a femoral stem design method including a data collection step of collecting femur data from a plurality of patients, a measurement standard setting step of setting a standard for designing a femoral stem with respect to the femur data of the plurality of patients collected in the data collection step, a measurement step of measuring a predetermined part of the femur from the femur data of the plurality of patients, a dimension determination step of determining a dimension of each part of a plurality of implants to be inserted into the femur, and a shape determination step of determining shapes of the plurality of implants according to the dimension of the plurality of implants determined in the dimension determination step, in which the measurement standard setting step includes a boundary setting step of setting a boundary that distinguishes the cortical bone and the cancellous bone from the femur data of the plurality of patients, and an axis setting step of setting an axis extending from the proximal part to the distal part of the femur. Thereby, during the design of an artificial femoral stem to be inserted into the femur in surgical procedures such as hip arthroplasty, data analysis is quickly carried out by using minimal anatomical data through a patient's 2D-based human anatomical information, and implants are designed to have regular shapes corresponding to the anatomical shape of the patient's femur.

Another objective of the present disclosure is to provide a femoral stem design method for designing implants by measuring minimal anatomical data, in which the measurement step includes a step of measuring a width from the axis to a lateral boundary at a position spaced by a predetermined distance proximally apart from the lesser trochanter of the femur along the axis, a step of measuring a width from the axis to a medial boundary, and a step of measuring a width from the medial boundary to the lateral boundary at a position spaced by a predetermined distance distally apart from the lesser trochanter of the femur.

Another objective of the present disclosure is to provide a femoral stem design method for providing a plurality of implants having sizes corresponding to patient's femur data, in which the dimension determination step includes a step of determining a plurality of proximal widths on the basis of the widths from the axis to the lateral boundary and the medial boundary measured in the measurement step and a step of determining a plurality of distal widths on the basis of the width from the medial boundary to the lateral boundary; and the plurality of proximal widths and the plurality of distal widths determined in the dimension determination step gradually increase or decrease.

Another objective of the present disclosure is to provide a femoral stem design method, in which the plurality of proximal widths and the plurality of distal widths determined in the dimension determination step increase or decrease at regular intervals, thereby enabling standardization of dimensions.

Another objective of the present disclosure is to provide a femoral stem design method, in which the dimension determination step further includes a step of determining lengths of the plurality of implants so that the lengths of the implants change in proportion to the determined proximal widths.

Another objective of the present disclosure is to provide a femoral stem design method, in which the shape determination step determines the shapes of the implants so that a medial part of each of the implants increases as a size of the implant increases; the shape determination step includes a standard setting step for setting a part serving as a standard for determining the shapes of the implants, a medial curvature determination step of determining a curvature of the medial part extending distally in a curve from a medial end of each of the implants, and an extension length determination step of determining a length of the curvature portion extending distally with the curvature from the medial end; and the shapes of the implants are determined to correspond to the anatomical shape of the inside of the femur.

Another objective of the present disclosure is to provide a femoral stem design method, in which the medial curvature determination step determines the curvature so that respective curvature portions of the plurality of implants extend with the same curvature to have different shapes according to sizes of the implants.

Another objective of the present disclosure is to provide a femoral stem design method, in which the extension length determination step determines a plurality of extension lengths so that lengths of the curvature portions increase as the proximal widths of the implants increase, whereby the medial boundary of the femur and the implants have a complementary shape.

Another objective of the present disclosure is to provide a femoral stem design method, in which the shape determination step further includes a connection portion curve determination step of determining a shape from an end of the curvature portion to an end of a distal part of each of the implants, and the connection portion curve determination step determines a shape from a distal end of the curvature portion to the end of the distal part of the implant to correspond to the anatomical shape of the inside of the femur.

Another objective of the present disclosure is to provide a femoral stem design method, in which the standard setting step sets the axis and the lesser trochanter as the standard so that the shapes of the plurality of implants are determined to be aligned with respect to the axis and the lesser trochanter.

Technical Solution

In order to accomplish the above objectives, the present disclosure is realized by embodiments having the following configuration.

According to one embodiment of the present disclosure, a femoral stem design method may include: a data collection step of collecting femur data from a plurality of patients; a measurement standard setting step of setting a standard for designing a femoral stem with respect to the femur data of the plurality of patients collected in the data collection step; a measurement step of measuring a predetermined part of the femur from the femur data of the plurality of patients; a dimension determination step of determining a dimension of each part of a plurality of implants to be inserted into the femur; and a shape determination step of determining shapes of the plurality of implants according to the dimension of the plurality of implants determined in the dimension determination step. Here, the measurement standard setting step may include: a boundary setting step of setting a boundary that distinguishes the cortical bone and the cancellous bone from the femur data of the plurality of patients; and an axis setting step of setting an axis extending from the proximal part to the distal part of the femur.

According to another embodiment of the present disclosure, the measurement step may include: a step of measuring a width from the axis to a lateral boundary at a position spaced by a predetermined distance proximally apart from the lesser trochanter of the femur along the axis; a step of measuring a width from the axis to a medial boundary; and a step of measuring a width from the medial boundary to the lateral boundary at a position spaced by a predetermined distance distally apart from the lesser trochanter of the femur.

According to another embodiment of the present disclosure, the measurement step may further include a step of measuring a distance from the axis to a center of the femoral head and a distance from the lesser trochanter to the center of the femoral head.

According to another embodiment of the present disclosure, the dimension determination step may include: a step of determining a plurality of proximal widths on the basis of the widths from the axis to the lateral boundary and the medial boundary measured in the measurement step; and a step of determining a plurality of distal widths on the basis of the width from the medial boundary to the lateral boundary, and the determined plurality of proximal widths and plurality of distal widths determined in the dimension determination step may gradually increase or decrease.

According to another embodiment of the present disclosure, the plurality of proximal widths and the plurality of distal widths determined in the dimension determination step may increase or decrease at regular intervals.

According to another embodiment of the present disclosure, the dimension determination step may further include a step of determining lengths of the plurality of implants so that the lengths of the implants change in proportion to the determined proximal widths.

According to another embodiment of the present disclosure, the shape determination step may determine the shapes of the implants so that a medial part of each of the implants increases as a size of the implant increases, and the shape determination step may include: a standard setting step for setting a part serving as a standard for determining the shapes of the implants; a medial curvature determination step of determining a curvature of the medial part extending distally in a curve from a medial end of each of the implants; and an extension length determination step of determining a length of the curvature portion extending distally with the curvature from the medial end.

According to another embodiment of the present disclosure, the medial curvature determination step may determine the curvature so that respective curvature portions of the plurality of implants extend with the same curvature.

According to another embodiment of the present disclosure, the extension length determination step may determine a plurality of extension lengths so that lengths of the curvature portions increase as the proximal widths of the implants increase.

According to another embodiment of the present disclosure, the shape determination step may further include a connection portion curve determination step of determining a shape from an end of the curvature portion to an end of a distal part of each of the implants.

According to another embodiment of the present disclosure, the connection portion curve determination step may determine the shape from a distal end of the curvature portion to the end of the distal part of the implant to correspond to an anatomical shape of the inside of the femur.

According to another embodiment of the present disclosure, the standard setting step may set the axis and the lesser trochanter as the standard so that the shapes of the plurality of implants are determined to be aligned with respect to the axis and the lesser trochanter.

Advantageous Effects

The present disclosure having the above configuration has the following effects.

According to the present disclosure, it is possible to provide a femoral stem design method including a data collection step of collecting femur data from a plurality of patients, a measurement standard setting step of setting a standard for designing a femoral stem with respect to the femur data of the plurality of patients collected in the data collection step, a measurement step of measuring a predetermined part of the femur from the femur data of the plurality of patients, a dimension determination step of determining a dimension of each part of a plurality of implants to be inserted into the femur, and a shape determination step of determining shapes of the plurality of implants according to the dimension of the plurality of implants determined in the dimension determination step, in which the measurement standard setting step includes a boundary setting step of setting a boundary that distinguishes the cortical bone and the cancellous bone from the femur data of the plurality of patients, and an axis setting step of setting an axis extending from the proximal part to the distal part of the femur. Thereby, during the design of an artificial femoral stem to be inserted into the femur in surgical procedures such as hip arthroplasty, data analysis is quickly carried out by using minimal anatomical data through a patient's 2D-based human anatomical information, and implants are designed to have regular shapes corresponding to the anatomical shape of the patient's femur.

According to the present disclosure, it is possible to provide a femoral stem design method, in which the measurement step includes a step of measuring a width from the axis to a lateral boundary at a position spaced by a predetermined distance proximally apart from the lesser trochanter of the femur along the axis, a step of measuring a width from the axis to a medial boundary, and a step of measuring a width from the medial boundary to the lateral boundary at a position spaced by a predetermined distance distally apart from the lesser trochanter of the femur. Thereby, implants can be designed on the basis of minimal anatomical data.

According to the present disclosure, it is possible to provide a femoral stem design method, in which the dimension determination step includes a step of determining a plurality of proximal widths on the basis of the widths from the axis to the lateral boundary and the medial boundary measured in the measurement step and a step of determining a plurality of distal widths on the basis of the width from the medial boundary to the lateral boundary; and the plurality of proximal widths and the plurality of distal widths determined in the dimension determination step gradually increase or decrease. Thereby, a plurality of implants having sizes corresponding to patient's femur data can be provided.

According to the present disclosure, it is possible to provide a femoral stem design method, in which the plurality of proximal widths and the plurality of distal widths determined in the dimension determination step increase or decrease at regular intervals, thereby enabling standardization of dimensions.

According to the present disclosure, it is possible to provide a femoral stem design method, in which the dimension determination step further includes a step of determining lengths of the plurality of implants so that the lengths of the implants change in proportion to the determined proximal widths.

According to the present disclosure, it is possible to provide a femoral stem design method, in which the shape determination step determines the shapes of the implants so that a medial part of each of the implants increases as a size of the implant increases; the shape determination step includes a standard setting step for setting a part serving as a standard for determining the shapes of the implants, a medial curvature determination step of determining a curvature of the medial part extending distally in a curve from a medial end of each of the implants, and an extension length determination step of determining a length of the curvature portion extending distally with the curvature from the medial end; and the shapes of the implants are determined to correspond to the anatomical shape of the inside of the femur.

According to the present disclosure, it is possible to provide a femoral stem design method, in which the medial curvature determination step determines the curvature so that respective curvature portions of the plurality of implants extend with the same curvature to have different shapes according to sizes of the implants.

According to the present disclosure, it is possible to provide a femoral stem design method, in which the extension length determination step determines a plurality of extension lengths so that lengths of the curvature portions increase as the proximal widths of the implants increase, whereby the medial boundary of the femur and the implants have a complementary shape.

According to the present disclosure, it is possible to provide a femoral stem design method, in which the shape determination step further includes a connection portion curve determination step of determining a shape from an end of the curvature portion to an end of a distal part of each of the implants, and the connection portion curve determination step determines a shape from a distal end of the curvature portion to the end of the distal part of the implant to correspond to the anatomical shape of the inside of the femur.

According to the present disclosure, it is possible to provide a femoral stem design method, in which the standard setting step sets the axis and the lesser trochanter as the standard so that the shapes of the plurality of implants are determined to be aligned with respect to the axis and the lesser trochanter.

BEST MODE

Hereinafter, a femoral stem design method according to the present disclosure will be described in detail with reference to the accompanying drawings. Unless otherwise defined, all terms including technical and scientific terms used herein have the same meaning as commonly understood by one of ordinary skill in the art to which the present disclosure belongs. When terms used herein conflicts with the commonly understood meaning, the terms will be interpreted as defined herein. Further, a detailed description of related known configurations or functions may be omitted to avoid obscuring the subject matter of the present disclosure.

It will be understood that when an element is referred to as being "connected" to another element, it can be directly connected to the other element or can be indirectly connected such as by bolts, nuts, and screws, or intervening elements may be present therebetween. Reference will now be made in greater detail to an exemplary embodiment of the present disclosure, examples of which are illustrated in the accompanying drawings.

Figure 3:
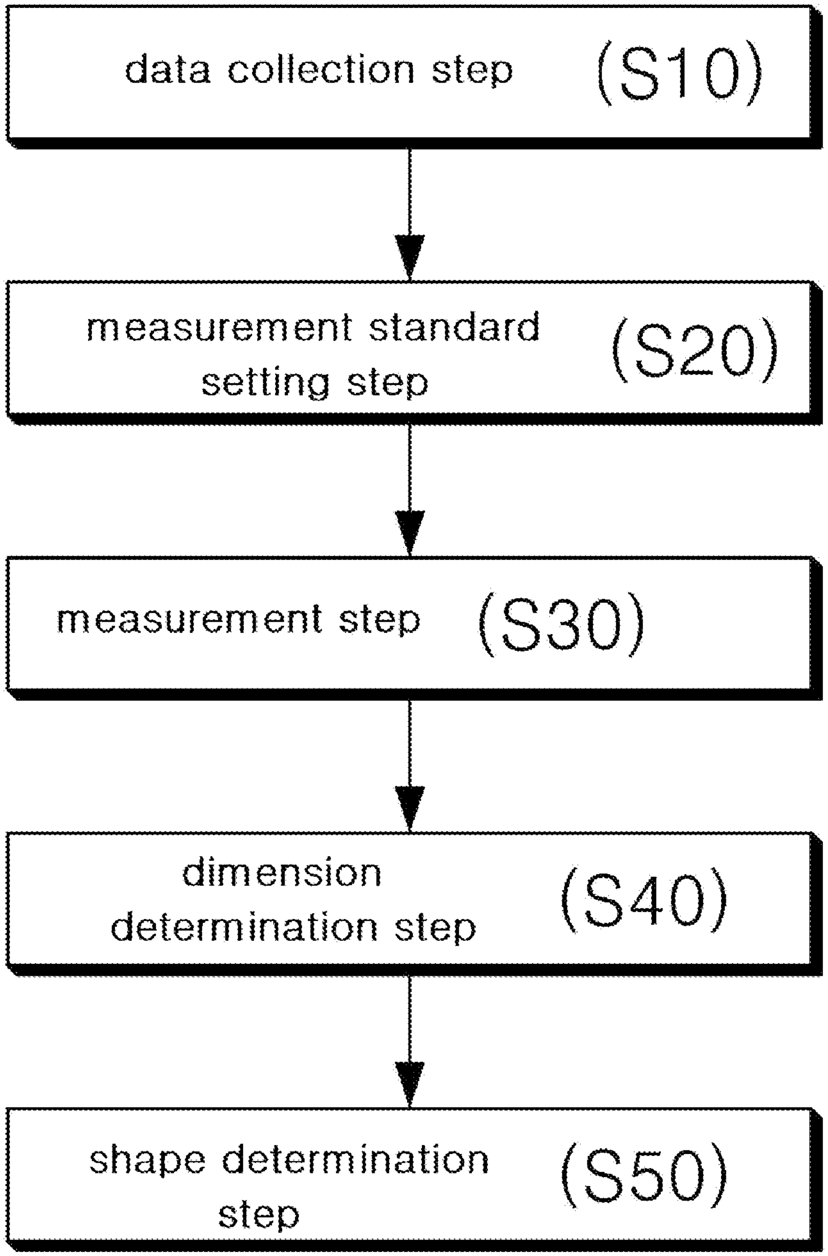
FIG. 3 is a flowchart illustrating a femoral stem design method according to an embodiment of the present disclosure.

FIG. 3 is a flowchart illustrating a femoral stem design method according to an embodiment of the present disclosure. Referring to FIG. 3, the femoral stem design method is characterized in that during the design of an artificial femoral stem to be inserted into the femur in surgical procedures such as hip arthroplasty, data analysis is quickly carried out by using minimal anatomical data through a patient's 2D-based human anatomical information, and implants are designed to have regular shapes corresponding to the anatomical shape of the patient's femur. The femoral stem design method includes a data collection step S10, a measurement standard setting step S20, a measurement step S30, a dimension determination step S40, and a shape determination step S50.

Figure 1:
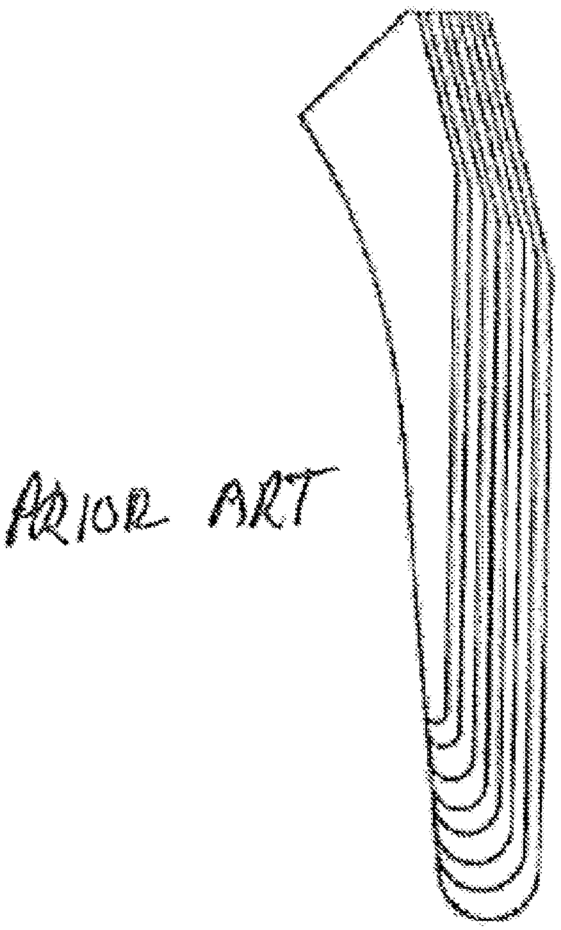
FIG. 1 is a view illustrating a femoral stem implant set according to the prior art.
Figure 2:
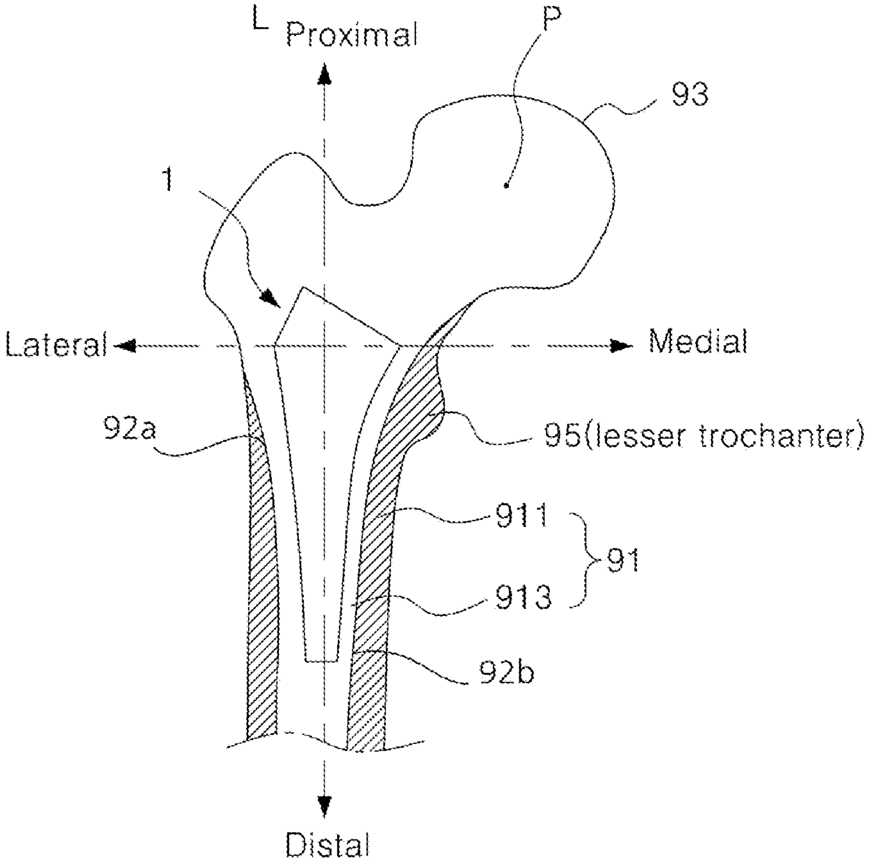
FIG. 2 is a view illustrating a femoral stem implant inserted into the femur.

In the data collection step S10, femur information is collected from a plurality of patients. The data collection step S10 collects 3D or 2D anatomical data of the femur by means of MRT, CT, X-rays, etc. through medical equipment. The anatomical data of the femur is collected from a sufficient number of patients of at least 100, 200, or 500. In an embodiment of the present disclosure, the data collection step S10 collects 2D femur data of the patients. Here, as illustrated in FIG. 2, the 2D femur data of the patients is obtained along a coronal plane so that the medial, lateral, proximal, and distal sides of the femur can be distinguished. By obtaining the 2D femur data of the patients in the data collection step S10, it is possible to quickly and economically design an implant to be inserted into the femur with only a small amount of data, unlike analysis using 3D data and femoral stem or implant design.

Figure 4:
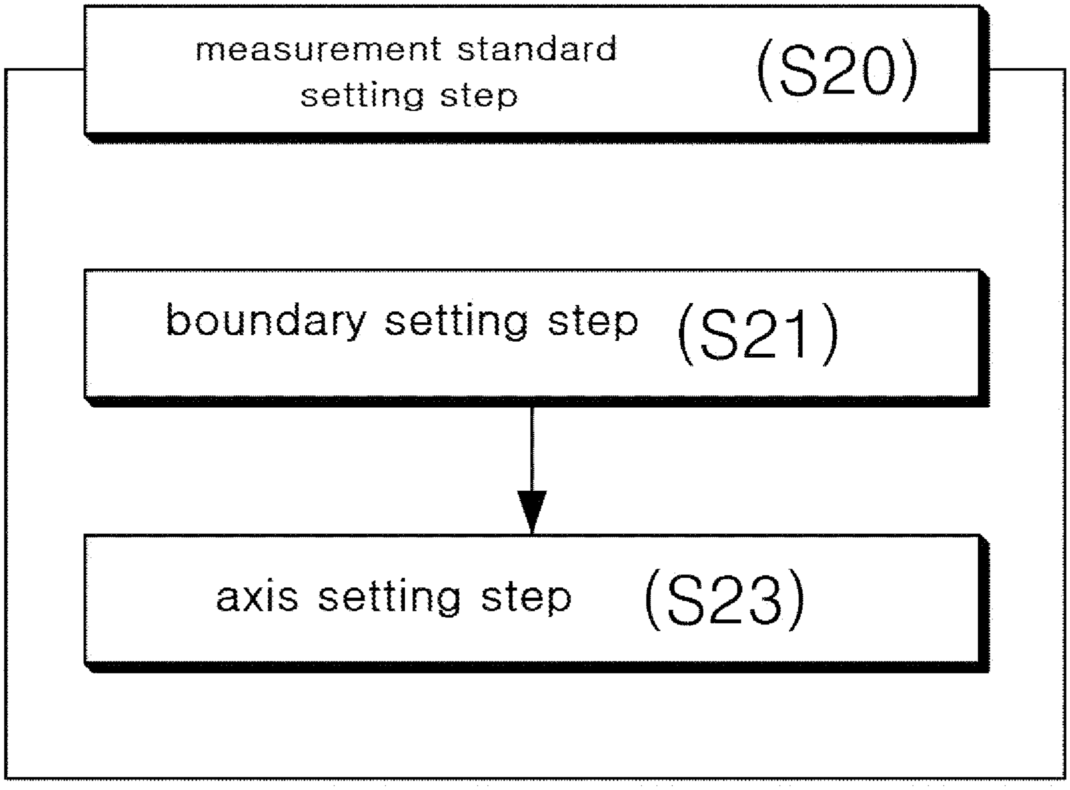
FIG. 4 is a flowchart illustrating a measurement standard setting step according to an embodiment of the present disclosure.

FIG. 4 is a flowchart illustrating a measurement standard setting step S20 according to an embodiment of the present disclosure. The measurement standard setting step S20 is a step of setting a standard for designing a femoral stem with respect to the femur data of the patients collected in the data collection step S10. In order to measure each dimension in the 2D femur data of the patients and determine the shape of the implant, standards for measurement, such as axis or boundary, are required. The measurement standard setting step S20 includes a boundary setting step S21 and an axis setting step S23.

In the boundary setting step S21, a boundary that divides the cortical bone and the cancellous bone is set from the femur data of the patients. In the 2D femur data of the patients, for example, a 2D image obtained through X-rays, the cortical bone and the cancellous bone are distinguished according to brightness. As illustrated in FIG. 2, the cortical bone 911 is located in the outer layer of the bone and is a hard area with no cavity. The cancellous bone 913 is located inside the cortical bone 911, and consists of bony trabeculae, and marrow cavities that contain adipose tissue or hematopoietic tissue. As described above, for insertion of a femoral stem in artificial hip arthroplasty, the relatively hard cancellous bone is removed, and then the femoral stem is inserted into the cavity in the femur. Therefore, in the boundary setting step S21, a boundary 92 is set between the cortical bone and the cancellous bone to divide the cortical bone and the cancellous bone. By the boundary setting step S21, a lateral boundary 92*a* and a medial boundary 92*b* are set. The lateral boundary 92*a* is a boundary formed on the lateral side of the femur, i.e., the part facing the outside of the human body, and the medial boundary 92*b* is a boundary formed on the medial side of the femur, i.e., the part facing the inside of the human body.

In the axis setting step S23, an axis L extending from the proximal part to the distal part of the femur is set. The axis set by the axis setting step S23 corresponds to the anatomical axis of the femur, and may extend from the center of the isthmus of the distal part of the femur along the mechanical axis. Preferably, the axis is determined to extend from the center of the cancellous bone region along the mechanical axis at a position spaced by a predetermined distance apart from the lesser trochanter toward the distal side. As the axis L is determined, the design of the implant is performed on the basis of the axis in a measurement step S30 and a shape determination step S50, which will be described later.

Figure 5:
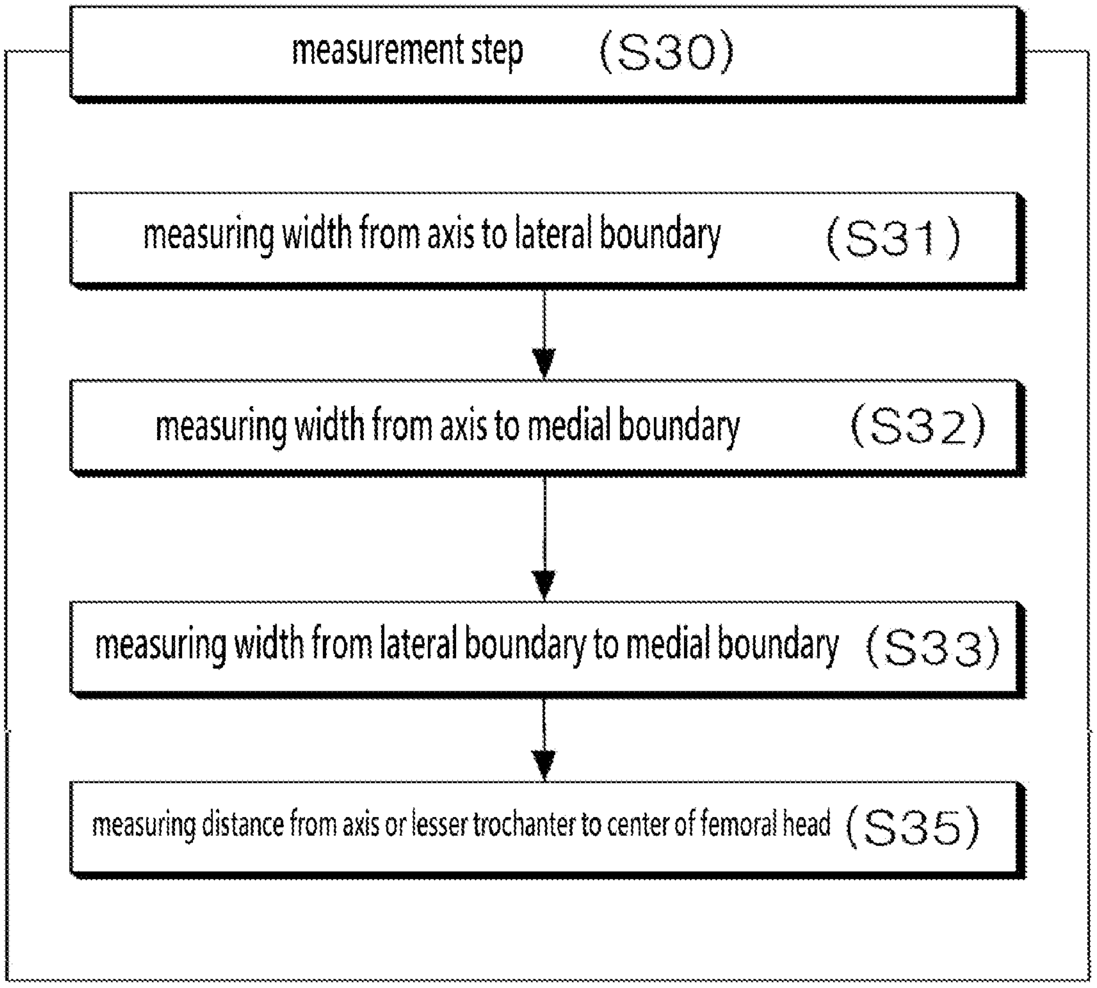
FIG. 5 is a flowchart illustrating a measurement step according to an embodiment of the present disclosure.
Figure 6:
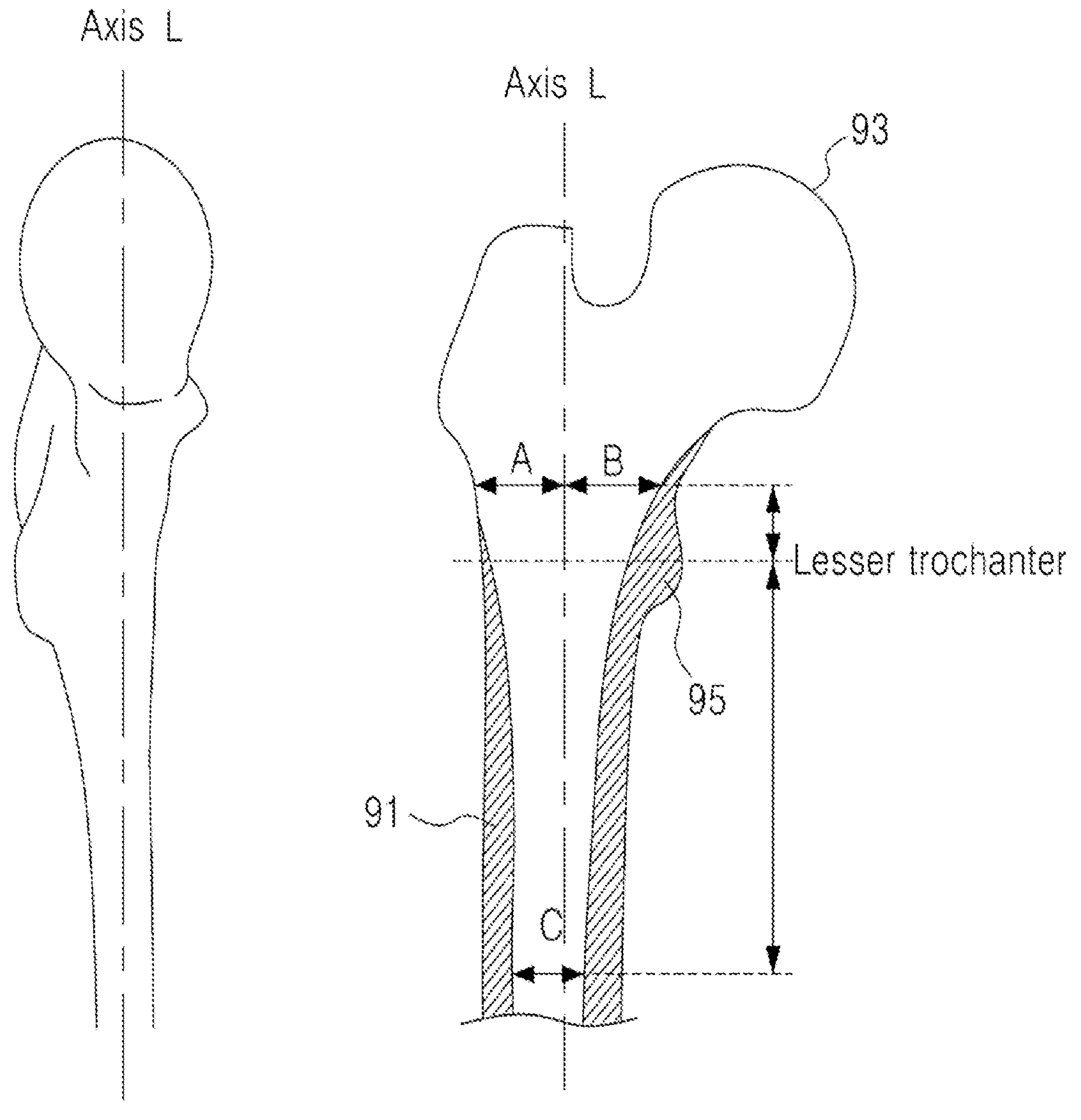
FIG. 6 is a view illustrating measuring a width from an axis to a boundary in the measurement step of the present disclosure.
Figure 7:
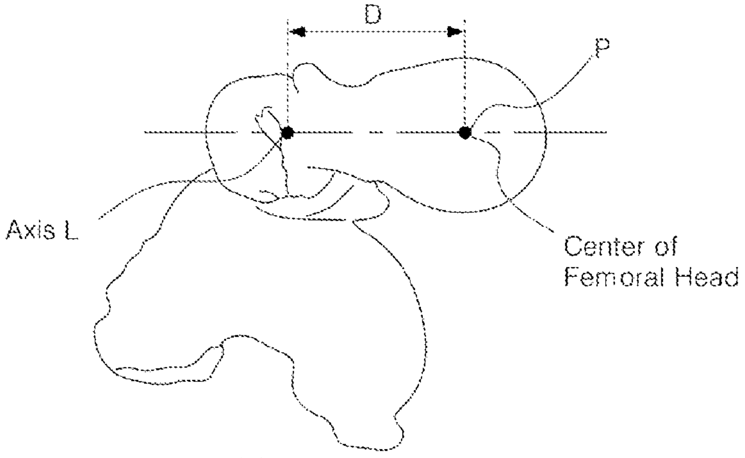
FIG. 7 is a view illustrating measuring a distance from the axis to the femoral head.
Figure 7:
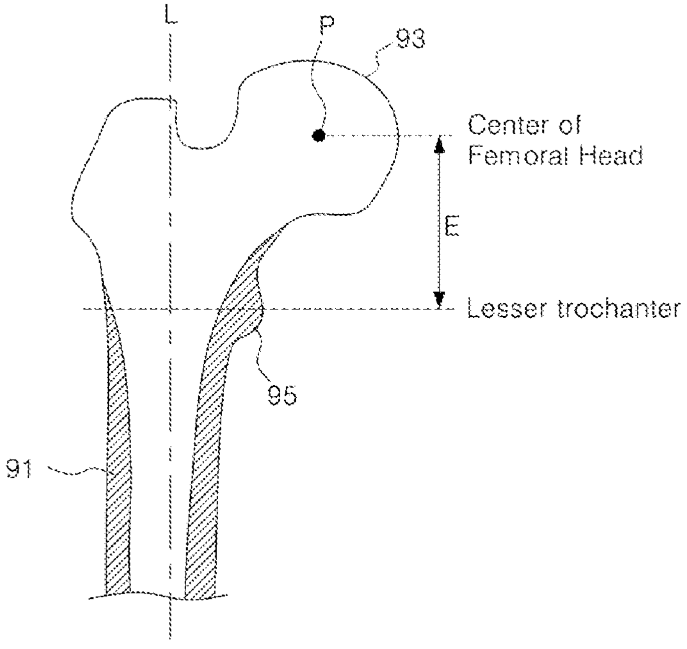

FIG. 5 is a flowchart illustrating a measurement step S30 according to an embodiment of the present disclosure. FIG. 6 is a view illustrating measuring a width from an axis to a boundary in the measurement step S30 of the present disclosure. FIG. 7 is a view illustrating measuring a distance from the axis to the femoral head. Referring to FIGS. 5 to 7, the measurement step S30 is a step of measuring a predetermined part of the femur from a plurality of femur data, and measures dimensions necessary for designing the femoral stem, i.e., the implant to be inserted into the femur. According to the related art, an implant is designed by setting cross-sections of patient's 3D femur data at regular intervals, for example, at intervals of 10 to 20 mm, measuring various dimensions in the cross-sections, and collecting the data. As described above, this method is difficult and slow to process information due to a large amount of data generated in the measurement process, and is uneconomical in designing the implant. In the measurement step S30 of the present disclosure, only data of an essential part for designing the size and shape of the implant is measured, and the shape of the implant is designed to correspond to the anatomical shape of the inner surface of the patient's femur, thereby achieving economic feasibility and convenience. The measurement step S30 includes a step S31 of measuring a width from the axis to the lateral boundary, a step S32 of measuring a width from the axis to the medial boundary, and a step S33 of measuring a width from the medial boundary to the lateral boundary at a position spaced apart from the lesser trochanter toward the distal side.

As illustrated in FIG. 6, the step S31 of measuring the width from the axis to the lateral boundary is performed for designing a proximal part of the implant, and measures a width A from the axis L to the lateral boundary 92*a* at a position spaced by a predetermined distance proximally apart from the lesser trochanter 95 along the axis. The step S32 of measuring the width from the axis to the medial boundary measures a width B from the axis L to the medial boundary 92*b*. The widths A and B may be measured at positions spaced by a distance of 5 mm, 10 mm, 15 mm, or 20 mm proximally apart from the lesser trochanter 95, preferably at a position spaced by a distance of 5 to 15 mm apart from the lesser trochanter. In addition, in another embodiment of the present disclosure, a distance (A+B) from the lateral boundary 92*a* to the medial boundary 92*b* may be measured at a position spaced by a predetermined distance proximally apart from the lesser trochanter, instead of measuring the distance from the axis to the boundary. Preferably, the measurement is made in a direction orthogonal to the axis.

The step S33 of measuring the width from the medial boundary to the lateral boundary at a position spaced apart from the lesser trochanter toward the distal side is performed for designing a distal part of the implant, and measures a width C between the lateral boundary 92*a* and the medial boundary 92*b* at a position spaced apart from the lesser trochanter 95 toward the distal side. The width C may be measured at positions spaced by a distance of 40 mm, 50 mm, 60 mm, or 70 mm apart from the lesser trochanter 95 toward the distal side, preferably, at a position spaced by a distance of 50 to 70 mm apart from the lesser trochanter.

The measurement step S30 may further include a step S35 of measuring a distance from the axis L or the lesser trochanter 95 to a center P of the femoral head. The step S35 is performed to determine the size and position of the acetabular cup connected to the femoral stem, and may also be performed to determine the shape or angle of the proximal part of the implant. Here, the shape of the medial side of a proximal part 11 of an implant 1 which will be described later may be determined. As illustrated in FIG. 7(*a*), a distance D from the axis L to the center P of the femoral head may be measured, and as illustrated in FIG. 7(*b*), a distance from the lesser trochanter 95 to the center P of the femoral head along the axis may be measured.

Figure 8:
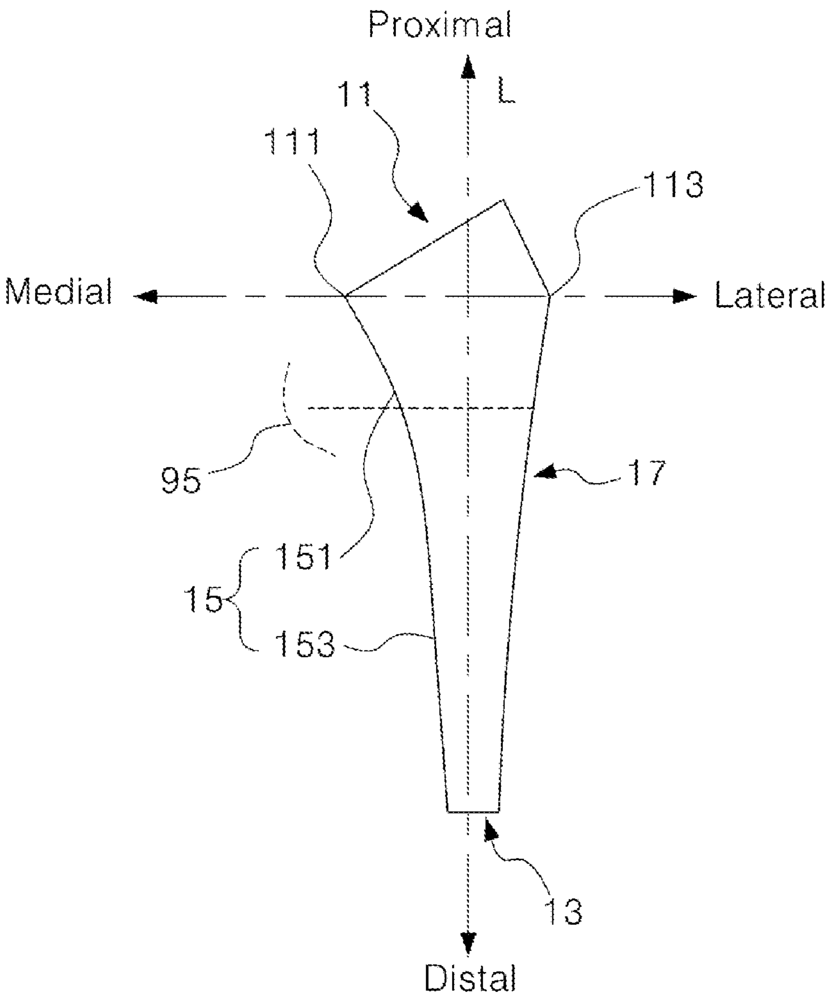
FIG. 8 is a view illustrating an implant according to the present disclosure.
Figure 9:
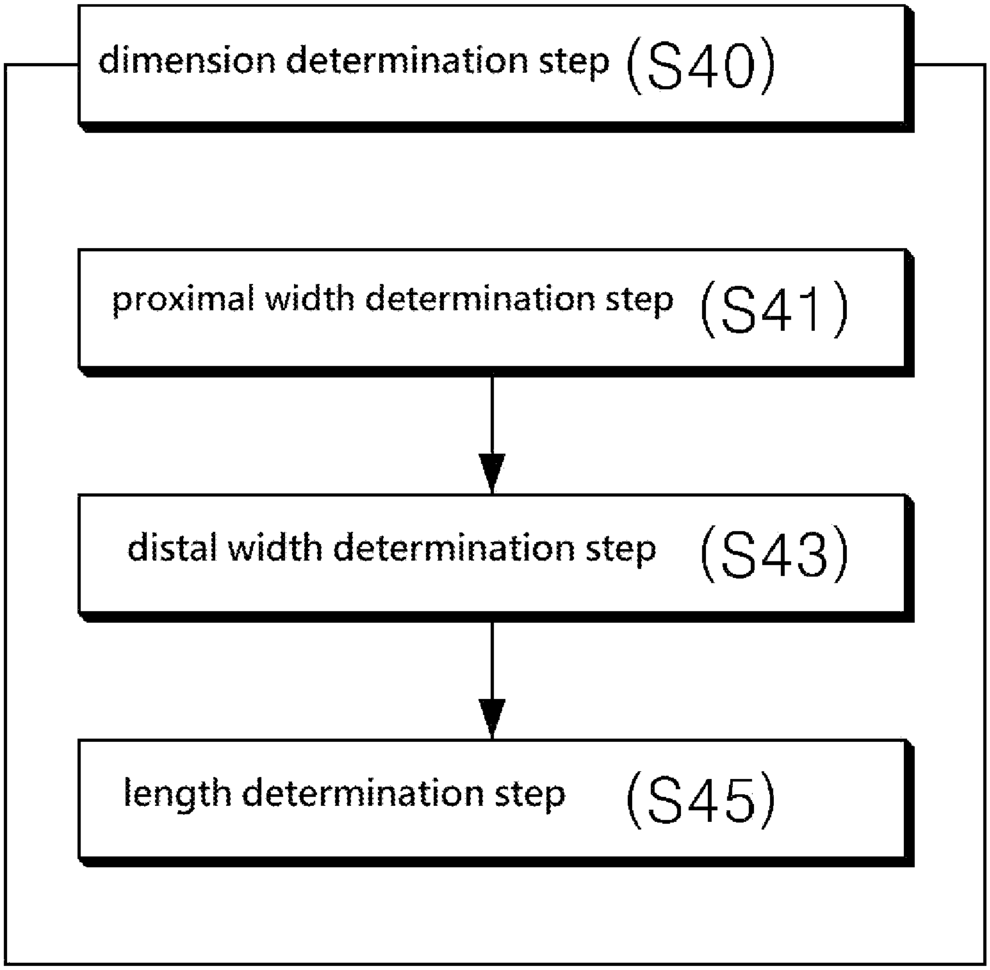
FIG. 9 is a flowchart illustrating a dimension determination step according to an embodiment of the present disclosure.

Referring to FIGS. 8 and 9, in the dimension determination step S40, a dimension of each part of a plurality of implants to be inserted into the femur is determined. Since the size of the femur is different for each patient and the size of an implant suitable for each patient changes according to the size of the femur, the femoral stem design method according to the present disclosure designs implants of various sizes. In the dimension determination step S40, the dimension of each part of the implants is determined. Here, a plurality of dimensions are determined for each part to design implants corresponding to the anatomical shape of the each patient's femur.

The implant 1, the shape of which is determined by the femoral stem design method according to the present disclosure, will be described with reference to FIGS. 2 and 8. As described above, the implant 1 is inserted into the patient's femur after removing the cancellous bone 913 of the femur. Here, it is preferable that the implant 1 is fixed in position within the patient's femur in correspondence with the inner shape of the patient's femur without shaking or rotating. The implant 1 includes the proximal part 11 located toward the pelvic bone after being inserted into the femur, a distal part 13 aligned distally, a medial part 15 located anatomically medially, and a lateral part 17 located anatomically laterally.

The proximal part 11 is defined as the proximal side of the implant, i.e., the upper part in FIG. 8, and corresponds to the proximal side of a medial point 111 located at a medial end of the implant. The proximal part 11 has a shape extending medially and laterally from a proximal end of the implant 1. The proximal part 11 has the medial point 111 located at the medial end of the implant, and a lateral point 113 formed on a line extending from the medial point 111 in a direction orthogonal to the axis at a height corresponding to the medial point. As will be described later, the lateral point 113 may correspond to a lateral end of the implant, but is not limited thereto. A distance from the medial point 111 to the lateral point 113 is defined as a proximal width, and a distance from the medial point 111 to the axis L is defined as a medial proximal width. The medial point 111 and the lateral point 113 are preferably formed on the proximal side at positions spaced by a predetermined distance apart from the lesser trochanter 95. The medial point 111 and the lateral point 113 may be spaced by a distance of 5 mm, 7.5 mm, 10 mm, 12.5 mm, or 15 mm apart from the lesser trochanter 95, but are not limited thereto, and the distance is preferably 7.5 to 12.5 mm. In addition, a plurality of proximal widths are determined to design a plurality of implants having different sizes.

The distal part 13 is defined as the distal side of the implant, i.e., the lower part in FIG. 8, and may be tapered toward a distal end of the implant to correspond to the shape of the femur. The distal end may be formed approximately orthogonal to the axis. Here, the width of the distal end is defined as a distal width. The center of the distal end is preferably formed to be aligned with the axis L and inserted into the femur. A plurality of distal widths are determined to design a plurality of implants having different sizes.

Furthermore, a distance extending from the medial point 111 or the lateral point 113 of the implant to the distal end along the axis is defined as an implant length. Here, a plurality of implant lengths are determined according to measured femur data so that implants corresponding to the size of each patient's femur are designed. Preferably, the implant length is determined to increase in proportion to the proximal width or the medial proximal width and the distal width.

The medial part 15 is a part that extends distally in a curve from the medial point 111 of the medial end. In order for the implant 1 to not change in position or shake within the femur, it is preferable that the shape of the implant 1 corresponds to the inner shape of the femur. As the medial part 15 extends in a curve, it has a shape corresponding to the medial boundary 92*b* of the femur. The medial part 15 includes a curvature portion 151 extending distally with a constant curvature from the medial point 111, and a connection portion 153 extending in a curve from an end of the curvature portion 151 to the distal end.

The curvature portion 151 extends distally with a constant curvature from the medial point 111. Here, at least a portion thereof may extend to the lesser trochanter 95. As the curvature portion 151 extends distally a constant curvature of R, an implant shape corresponding to the medial boundary 92*b* having a curved surface shape is formed. As will be described later, the extension length of the curvature portion 151 may change according to the size of the implant, i.e., the width of the proximal part 11 or the distal part 13 of the implant. Therefore, the shape of the medial part 15 changes as the size of the implant changes, so that implants corresponding to the anatomical shape of each patient's femur are designed.

The connection portion 153 is a portion connected from a distal end of the curvature portion 151 to an end of the distal part 13, and may be formed in a curved surface or curve shape. The connection portion 153 is determined depending on the length of the implant and the length of the curvature portion 151. Here, the shape of the connection portion 153 defined from the distal end of the curvature portion to the distal end of the implant is determined to correspond to the anatomical shape of the inside of the femur. Preferably, the shape corresponds to the shape of a logarithmic function ($y=x^{1/k}$) or an inverse function ($y=x^{-k}$) with the axis L as an asymptote.

Figure 10:
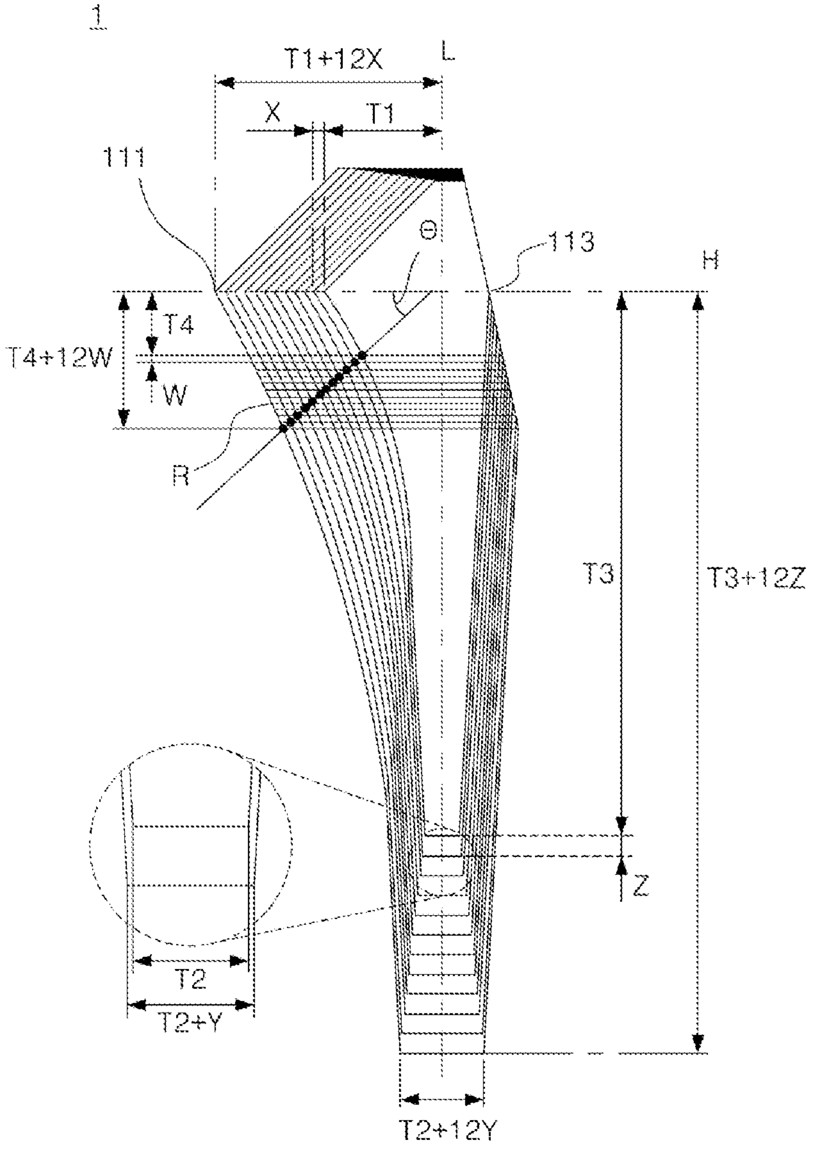
FIG. 10 is a view illustrating the dimensions and shapes of a plurality of implants according to the present disclosure.

As illustrated in FIGS. 8 and 10, the lateral part 17 is a part extending on the lateral side of the implant, and connects the lateral end and the distal end of the implant while forming a substantially straight line. In an embodiment of the present disclosure, the lateral end of the implant forming a proximal or lateral end of the straight lateral part may be formed at the lateral point 113, or may be formed on the distal side of the implant at a position spaced apart in proportion to the extension length of the curvature portion 151 from the lateral point 113. Although not illustrated, in another embodiment of the present disclosure, the lateral end of the implant may be formed at a position extending orthogonal to the axis from the distal end of the curvature portion 151 at a height corresponding to the distal end of the curvature portion 151.

Referring to FIG. 9 again, the dimension determination step S40 will be described. In the dimension determination step S40, the dimension of each part of the implant formed as described above is determined. Preferably, the proximal width, the medial proximal width, the distal width, and the implant length are determined. A plurality of dimensions are determined for each part of the implant in the dimension determination step S40 to design a plurality of implants having different sizes. The same numbers of proximal widths, distal widths, and implant lengths may be determined, but it is not excluded that different numbers of dimensions are determined. The dimension determination step S40 includes a proximal width determination step S41, a distal width determination step S43, and a length determination step S45.

Referring to FIG. 9, in the proximal width determination step S41, the proximal width of the implant is determined. In detail, a distance extending from the medial point 111 to the lateral point 113 in a direction orthogonal to the axis is determined. The proximal width is determined on the basis of data measured in the step S31 of measuring the width from the axis to the lateral boundary and the step S32 of measuring the width from the axis to the medial boundary. As the measurement is made on the basis of femur data of a plurality of patients, a plurality of proximal widths are determined. Here, the proximal widths may be determined to increase or decrease gradually and/or at regular intervals. In an embodiment of the present disclosure, a distance from the axis L to the lateral point 113 may be set to be constant, and the proximal width may be determined so that the medial proximal width increases or decreases. As illustrated in FIG. 10, in the case of an implant having a minimum size, the implant has a minimum medial proximal width $T_1$, and the medial proximal width increases by an interval of X ($T_1$+X) as the size of the implant increases. In an embodiment of the present disclosure, the number of the plurality of proximal widths may be 10, 11, 12, or 13, but is not limited thereto, and may be determined to be less than or greater than these numbers depending on the range of patient's femur data obtained.

In the distal width determination step S43, the distal width of the implant is determined. A plurality of distal widths are determined on the basis of the width from the medial boundary to the lateral boundary measured in the step S33 of measuring the width from the medial boundary to the lateral boundary at a position spaced apart from the lesser trochanter toward the distal side. As illustrated in FIG. 10, in the case of the implant having a minimum size, the implant has a minimum distal width $T_2$, and the distal width increases by an interval of Y ($T_2$+Y) as the size of the implant increases. In an embodiment of the present disclosure, the number of the plurality of distal widths may be 10, 11, 12, or 13, but is not limited thereto, and may be determined to be less than or greater than these numbers depending on the range of patient's femur data obtained.

The length determination step S45 is a step of determining a plurality of implant lengths defined as distances extending from the medial point 111 or the lateral point 113 to the distal end of the implant along the axis. In an embodiment of the present disclosure, in the length determination step S45, the implant lengths may be determined to change in proportion to the determined proximal widths or medial proximal widths. Therefore, as illustrated in FIG. 10, in the case of the implant having a minimum size, the implant has a minimum length $T_3$, and the length from the medial point 111 or the lateral point 113 to the distal end increases by an interval of Z ($T_3$+Z) as the size of the implant increases. In an embodiment of the present disclosure, the number of the plurality of implant lengths may be 10, 11, 12, or 13, but is not limited thereto, and may be determined to be less than or greater than these numbers depending on the range of patient's femur data obtained. In addition, in another embodiment of the present disclosure, the implant lengths may be determined to change in proportion to the average of the determined proximal widths or medial proximal widths and the distal widths, and the implant lengths may be determined independently of the proximal and distal widths according to the range of patient's femur data.

According to the above process, the dimensions of the implants are determined. In the dimension determination step S40, only the sizes of the implants are determined, but the shapes of the implants having the determined plurality of dimensions are not determined. The shape determination step S50 is performed to determine the shape of the implant according to the present disclosure so that the implant corresponds to the inner shape of the patient's femur, preferably so that the shape of the medial side of the implant changes as the size of the implant increases.

Figure 11:
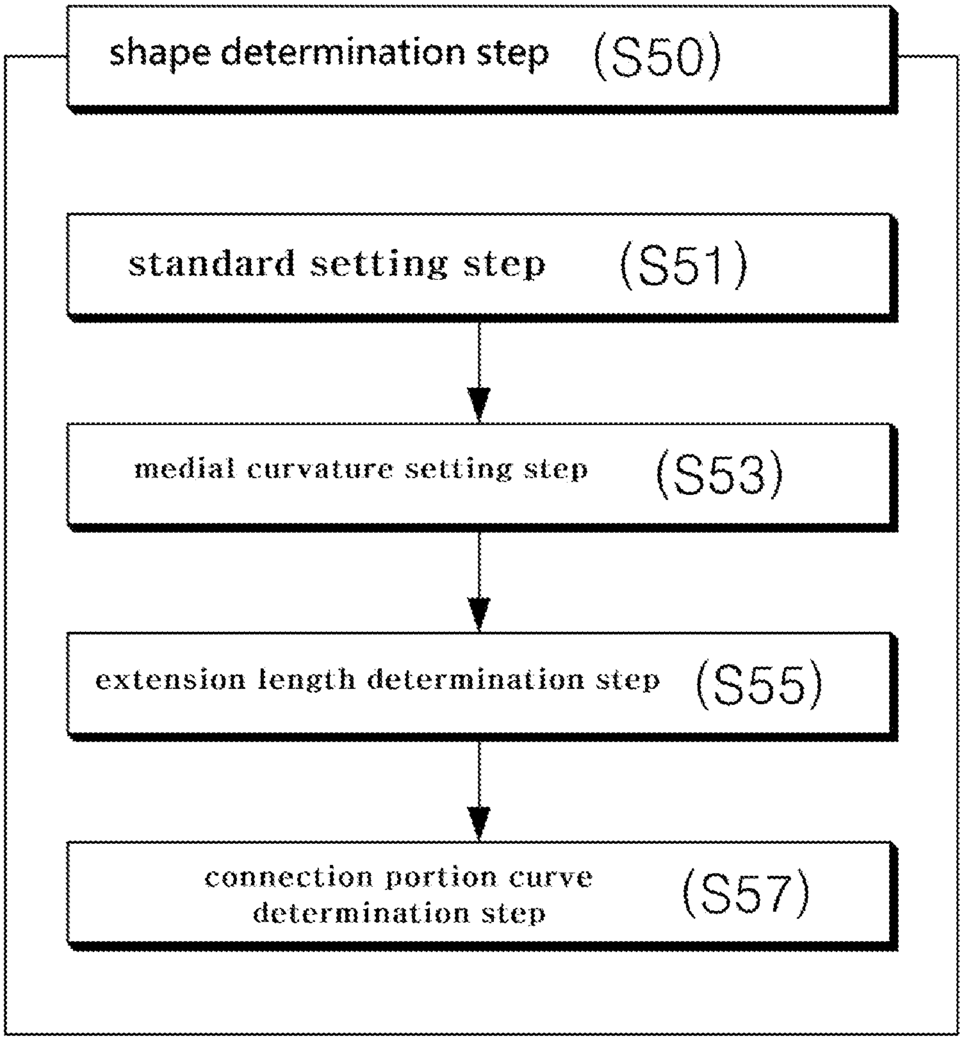
FIG. 11 is a flowchart illustrating a shape determination step according to an embodiment of the present disclosure.

Referring to FIG. 11, the shape determination step S50 is a step of determining shapes of the plurality of implants according to the dimensions of each part of the implants determined in the dimension determination step S40. In particular, the shapes of the implants are determined to correspond to the anatomical shape of each patient's femur by changing the shape of the medial part 15 of each of the implants. Preferably, the shape determination step S50 determines the shapes of the implants so that the size of the medial part of each of the implants increases as the size of the implant increases. The shape determination step S50 includes a standard setting step S51, a medial curvature setting step S53, an extension length determination step S55, and a connection portion curve determination step S57.

The standard setting step S51 is a step of setting a part that serves as a standard for determining the shapes of the implants. The axis L and/or the lesser trochanter 95 is set as the standard so that the shapes of the plurality of implants are aligned with respect to the axis L and/or the lesser trochanter 95. In detail, the center of the distal part 13 of each of the implants is aligned to be located on the axis, and the medial point 111 is formed to extend from the axis by the medial proximal width in a direction orthogonal to the axis. In addition, the medial point 111 and the lateral point 113 are formed on the proximal side at positions spaced by a predetermined distance apart from the lesser trochanter 95. Therefore, as illustrated in FIG. 10, it can be confirmed that the medial point 111 is spaced by a regular distance proximally apart from the lesser trochanter, and is spaced by the medial proximal width (i.e., the distance from the medial point to the axis L) from the axis. Thereby, the later point 113 formed at a height corresponding to the medial point on a line extending from the medial point 111 in a direction orthogonal to the axis maintains a constant position.

The medial curvature setting step S53 is a step of determining a curvature of the medial part extending distally in a curve from the medial end of the implant. As illustrated in FIGS. 8 and 10, the curvature portion 151 of the medial part extends distally with a constant curvature of R from the medial point 111. In the medial curvature determination step S53, the curvature is determined so that respective curvature portions of the plurality of implants extend with the same curvature of R. Thereby, respective medial parts 15 are designed to have different shapes according to the sizes of the implants. In another embodiment of the present disclosure, the curvature R may be set to change according to the width of the proximal width or the medial proximal width. The curvature is preferably determined to correspond to the anatomical shape of the medial boundary 92*b* of patient's femur data. The curvature R may be determined to have a radius of curvature of 100 mm, 105 mm, 110 mm, 115 mm, or 120 mm, but is not limited thereto.

In the extension length determination step S55, the extension length of the curvature portion 151 extending distally with the curvature from the medial end of the implant is determined. The extension length of the curvature portion 151 extending distally with a predetermined curvature R from the medial point 111 is determined so that at least a portion thereof extends to the lesser trochanter. Here, a plurality of extension lengths are determined to change according to the sizes of the implants. Therefore, as shown in FIG. 10, in the case of the implant having a minimum size, the curvature portion 151 extends with a minimum extension length T4 to a height where the lesser trochanter is located, and the extension length of the curvature portion 151 from the medial point 111 increases by an interval of W (T4+W) as the size of the implant increases. In an embodiment of the present disclosure, the number of the plurality of extension lengths may be 10, 11, 12, or 13, but is not limited thereto, and may be determined to be less than or greater than these numbers depending on the range of patient's femur data obtained.

In addition, in the extension length determination step 55, the length of the curvature portion 151 is may be determined to increase in proportion to the increase in the proximal with or the medial proximal width of the implant. Therefore, as illustrated in FIG. 10, the curvature portion 151 extends with a constant curvature to the point where the curvature portion 151 meets an oblique line extending at an angle of θ with a straight line H connecting the medial point 111 and the lateral point 113 to be orthogonal to the axis L. The curvature portion 151 may be designed to further extend at an interval of 1 mm, 1.5 mm, or 2 mm along the axis as the size of the implant increases.

The connection portion curve determination step S57 is a step of determining a shape from an end of the curvature portion 151 to an end of the distal part of the implant. The connection portion extends from the distal end of the curvature portion 151 to the end of the distal part 15, i.e., the medial end, of the implant in a shape different from that of the curvature portion 151 extending distally from the medial point 111. In the connection portion curve determination step S57, the shape from the distal end of the curvature portion to the end of the distal part of the implant, i.e., the shape of the connection portion 153, is determined to correspond to the anatomical shape of the inside of the femur. In detail, the shape of the connection portion 153 may be determined by taking an approximation of the femur data of the plurality of patients so that the connection portion 153 extends to the end of the distal part in a curve corresponding to the shape of a logarithmic function ($y=ax^{1/k}+b$) or an inverse function ($y=ax^{-k}+b$) with the axis L as an asymptote Although preferred embodiments of the present disclosure have been described for illustrative purposes, those skilled in the art will appreciate that various modifications, additions, and substitutions are possible, without departing from the scope and spirit of the present disclosure as disclosed in the accompanying claims.

The invention claimed is:

1. A femoral stem design method comprising:

a data collection step of collecting femur data obtained along a coronal plane from a plurality of patients;

a measurement standard setting step of setting a standard for designing a femoral stem with respect to the femur data of the plurality of patients collected in the data collection step;

a measurement step of measuring a predetermined part of the femur from the femur data of the plurality of patients;

a dimension determination step of determining a dimension of each part of a plurality of implants to be inserted into the femur; and a shape determination step of determining shapes of the plurality of implants according to the dimension of the plurality of implants determined in the dimension determination step, wherein the measurement standard setting step comprises:

a boundary setting step of setting a boundary that distinguishes the cortical bone and the cancellous bone from the femur data of the plurality of patients; and an axis setting step of setting an axis extending from the proximal part to the distal part of the femur, wherein the measurement step is performed by measuring only the following data of essential parts for designing a size and a shape of an implant:

a width from the axis to a lateral boundary at a first position spaced by a predetermined distance proximally apart from the lesser trochanter of the femur along the axis, for designing a proximal part of the implant;

a width from the axis to a medial boundary at the first position, for designing the proximal part of the implant; and a width from the medial boundary to the lateral boundary at a second position spaced by a predetermined distance distally apart from the lesser trochanter of the femur along the axis, for designing a distal part of the implant.

2. The femoral stem design method of claim 1, wherein the dimension determination step comprises a step of determining a plurality of proximal widths on the basis of the widths from the axis to the lateral boundary and the medial boundary measured in the measurement step, and the plurality of proximal widths determined in the dimension determination step gradually increase or decrease.

3. The femoral stem design method of claim 2, wherein the dimension determination step further comprises a step of determining a plurality of distal widths on the basis of the width from the medial boundary to the lateral boundary, and the determined plurality of distal widths gradually increase or decrease.

4. The femoral stem design method of claim 3, wherein the plurality of proximal widths and the plurality of distal widths determined in the dimension determination step increase or decrease at regular intervals.

5. The femoral stem design method of claim 2, wherein the dimension determination step further comprises a step of determining lengths of the plurality of implants so that the lengths of the implants change in proportion to the determined proximal widths.

6. The femoral stem design method of claim 2, wherein the shape determination step determines the shapes of the implants so that a medial part of each of the implants increases as a size of the implant increases, and the shape determination step comprises:

a standard setting step for setting a part serving as a standard for determining the shapes of the implants;

a medial curvature determination step of determining a curvature of the medial part extending distally in a curve from a medial end of each of the implants; and an extension length determination step of determining a length of the curvature portion extending distally with the curvature from the medial end.

7. The femoral stem design method of claim 6, wherein the medial curvature determination step determines the curvature so that respective curvature portions of the plurality of implants extend with the same curvature.

8. The femoral stem design method of claim 7, wherein the extension length determination step determines a plurality of extension lengths so that lengths of the curvature portions increase as the proximal widths of the implants increase.

9. The femoral stem design method of claim 8, wherein the shape determination step further comprises a connection portion curve determination step of determining a shape from an end of the curvature portion to an end of a distal part of each of the implants.

10. The femoral stem design method of claim 9, wherein the connection portion curve determination step determines the shape from a distal end of the curvature portion to the end of the distal part of the implant to correspond to an anatomical shape of the inside of the femur.

11. The femoral stem design method of claim 6, wherein the measurement standard setting step sets the axis and the lesser trochanter as the standard so that the shapes of the plurality of implants are determined to be aligned with respect to the axis and the lesser trochanter.

12. At least one implant having a shape determined by the femoral stem design method of claim 1.

* * * * *